(12) United States Patent
Yue et al.

(10) Patent No.: US 6,696,045 B2
(45) Date of Patent: Feb. 24, 2004

(54) DENTIFRICE COMPOSITIONS COMPRISING A STABLE LOW WATER, PHASE COMPRISING POLYPHOSPHATE AND IONIC ACTIVE INGREDIENTS

(75) Inventors: Jiang Yue, Beijing (CN); Long Zhu, Kobe Hyogo (JP); Li Chen, Beijing (CN); Ying Cheng, Beijing (CN); Tao Xu, Beijing (CN); Andrew Damian Weller, Mason, OH (US); Ying Wang, Rochester, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/302,031

(22) Filed: Nov. 22, 2002

(65) Prior Publication Data

US 2003/0124067 A1 Jul. 3, 2003

Related U.S. Application Data

(60) Provisional application No. 60/333,832, filed on Nov. 28, 2001.

(51) Int. Cl.$^7$ .............................. A61K 7/16; A61K 7/18
(52) U.S. Cl. .............................. 424/52; 424/49; 424/57
(58) Field of Search ..................................... 424/49–58

(56) References Cited

U.S. PATENT DOCUMENTS

| | | | |
|---|---|---|---|
| 4,647,541 A | 3/1987 | Guadagno et al. | |
| 5,670,137 A | 9/1997 | Ascione | |
| 5,939,052 A | 8/1999 | White, Jr. et al. | |
| 6,162,418 A | 12/2000 | Randive et al. | |
| 6,187,293 B1 | 2/2001 | Ballard | |
| 6,187,295 B1 | 2/2001 | Glandorf | |
| 6,190,644 B1 * | 2/2001 | McClanahan et al. | 424/52 |
| 6,350,436 B1 | 2/2002 | Glandorf et al. | |
| 6,521,216 B1 | 2/2003 | Glandorf et al. | |
| 6,555,094 B1 | 4/2003 | Glandorf et al. | |

FOREIGN PATENT DOCUMENTS

| | | |
|---|---|---|
| EP | 0638 307 B1 | 11/1997 |
| WO | WO 98/22079 | 5/1998 |
| WO | WO 98/22080 A1 | 5/1998 |
| WO | WO 01/68046 A2 | 9/2001 |

OTHER PUBLICATIONS

U.S. patent application Ser. No. 10/039,620, Glandorf et al., filed Oct. 24, 2001.
U.S. patent application Ser. No. 10/351,205, Glandorf et al., filed Jan. 24, 2003.
U.S. patent application Ser. No. 09/710,250, White, Jr. et al., filed Nov. 10, 2000.
U.S. patent application Ser. No. 10/319,108, Baig et al., filed Dec. 13, 2002.
U.S. patent application Ser. No. 09/831,462, Day et al., filed Jun. 22, 2000.
U.S. patent application Ser. No. 10/218,777, Yue et al., filed Aug. 14, 2002.
U.S. patent application Ser. No. 10/146,270, Day et al., filed May 15, 2002.
U.S. patent application Ser. No. 10/146,000, Lawlor, filed May 15, 2002.
U.S. patent application Ser. No. 10/146,258, Lawlor, filed May 15, 2002.
U.S. patent application Ser. No. 10/146,235, Lawlor, filed May 15, 2002.
U.S. patent application Ser. No. 10/146,698, Day et al., filed May 15, 2002.
U.S. patent application Ser. No. 09/489,310, Stephenson, filed Jan. 21, 2000.
U.S. patent application Ser. No. 10/318,963, Stephenson et al., filed Dec. 13, 2002.

* cited by examiner

Primary Examiner—Shep K. Rose
(74) Attorney, Agent, or Firm—Emelyn DeLeon Hiland

(57) ABSTRACT

Disclosed are dentifrice compositions comprising in a single phase: (a) from about 0.1% to about 30% of one or more linear polyphosphates having an average chain length of about 4 or more; (b) an ionic active ingredient selected from the group consisting of a fluoride ion source, a stannous ion source, a zinc ion source, a copper ion source and mixtures thereof, wherein the ionic active ingredient is present as a solid dispersion in the composition and delivers and effective amount of ionic active when solubilized; (c) a binder system comprised of (i) from about 0.05% to about 3% of a thickening agent selected from the group consisting of polysaccharides, carbomers, poloxamers, modified celluloses, and mixtures thereof; and (ii) from about 0.1% to about 70% of at least one humectant; wherein the dentifrice composition has a total water content of less than about 10%. Further disclosed are methods for stabilizing dentifrice compositions by providing such a binder system.

11 Claims, No Drawings

DENTIFRICE COMPOSITIONS COMPRISING A STABLE LOW WATER, PHASE COMPRISING POLYPHOSPHATE AND IONIC ACTIVE INGREDIENTS

CROSS REFERENCE RELATED TO APPLICATIONS

This application claims the benefit of U.S. Provisional Application No. 60/333,832, filed Nov. 28, 2001.

FIELD OF THE INVENTION

The present invention relates to dentifrice compositions comprising a low water phase comprising polyphosphate and ionic active ingredients including fluoride and/or metal ions such as stannous, zinc, and copper ions.

BACKGROUND OF THE INVENTION

The compositions of the present invention are dentifrices comprising a phase that provides effective amounts of polyphosphate and ionic actives such as fluoride ion and/or metal ions such as stannous, zinc, and copper ions, such a phase having a low level of water in which the components are stable, and also comprising a binder system that provides adequate gellation in a low water, non-polar humectant system.

While such actives have previously been used in dentifrices to promote oral health, for several reasons it has proven challenging to provide these actives together in a stable single phase. Certain polyphosphates effective as antitartar agents are known to be unstable in high aqueous systems and are also known to react with ionic fluoride in oral compositions at ambient temperature and produce monofluorophosphate ions, in addition to altering the pH of the composition. This reaction compromises the efficacy of the oral composition and its ability to provide stable ionic fluoride and polyphosphate to the oral surfaces.

Metal ions such as stannous, copper and zinc ions are known to be effective anti-microbial agents. These metal ions provide anti-gingivitis and anti-plaque benefits and may also improve breath and reduce sensitivity. However, dentifrices containing metal ions are also known to be astringent. Stannous and copper are also known to cause staining on the tooth surfaces.

Previous attempts to provide dentifrice compositions that contain these actives in efficacious amounts and in efficacious forms have provided the dentifrice in dual compartmented packaging wherein the reactive ingredients are kept physically separate until the time of brushing. (See, e.g., WO98/22079, "Dentifrice Compositions Containing Polyphosphate and Fluoride.") However, such dual-compartmented packages are typically considerably more expensive than the conventional laminate tubes that have been used for many years to contain and dispense dentifrices. They may also be problematic in terms of ease of consumer use and uniform dispensing of approximately equal amounts of each composition during each consumer use. Therefore it remains desirable to provide single phase compositions that can be packaged in conventional laminate squeeze tubes.

Other attempts to provide such efficacious dentifrice compositions have reduced the amount of water present in the composition. Reducing the amount of water would theoretically reduce or eliminate the stability issues associated with the fluoride, polyphosphate and other ionic actives. However, reducing the level of water, and optionally replacing some or all of the removed water with a humectant, creates problems in obtaining acceptable rheology and thickening properties in the composition. When water, which is a highly polar solvent, is removed, conventional thickening agents such as carboxymethylcellulose ("CMC") tend to inadequately gel up. Attempts to reduce water content in dentifrice have included the dentifrices described in, e.g., EP 0 638 307 B1; U.S. Pat. No. 4,647,451; and U.S. Pat. No. 5,670,137.

Carageenan, a polysaccharide and a natural derivative of seaweed, has been used in dentifrice compositions as a replacement for lower cost thickeners such as CMC. See, e.g., U.S. Pat. No. 6,187,293 B1, "Process For Making Toothpaste Using Low Levels of Carageenan," and U.S. Pat. No. 6,162,418, "Non-Stringy Toothpaste." However, the relatively higher cost of carageenan and the thixotropic properties of carageenen-containing toothpastes have been seen as limiting the widespread use of carageenen in dentifrices.

Therefore, it remains desirable to provide dentifrice compositions that provide efficacious delivery of water-unstable actives and/or actives that are reactive with respect to each other in a stable single phase. None of the existing art provides all of the advantages and benefits of the present invention.

SUMMARY OF THE INVENTION

The present invention relates to dentifrice compositions comprising in a single phase: (a) from about 0.1% to about 30% of one or more linear polyphosphates having an average chain length of about 4 or more; (b) an ionic active ingredient selected from the group consisting of a fluoride ion source, a stannous ion source, a zinc ion source, a copper ion source, and mixtures thereof, wherein the ionic active ingredient is present as a solid dispersion in the composition and delivers an effective amount of ionic active when solubilized; (c) a binder system comprised of (i) from about 0.05% to about 3% of a thickening agent selected from the group consisting of polysaccharides, carbomers, poloxamers, modified celluloses, and mixtures thereof; and (ii) from about 0.1% to about 70% of at least one humectant; wherein the dentifrice composition has a total water content of less than about 10%. The present invention further relates to methods for stabilizing dentifrice compositions by providing such a binder system. These and other features, aspects, and advantages of the invention will become evident to those of skill in the art from a reading of the present disclosure.

DETAILED DESCRIPTION OF THE INVENTION

While the specification concludes with claims particularly pointing out and distinctly claiming the invention, it is believed that the present invention will be better understood from the following description of preferred embodiments.

All percentages used herein are by weight of the dentifrice composition, unless otherwise specified. The ratios used herein are molar ratios of the overall composition, unless otherwise specified. All measurements are made at 25° C., unless otherwise specified.

All publications, patent applications, and issued patents mentioned herein are hereby incorporated in their entirety by reference. Citation of any reference is not an admission regarding any determination as to its availability as prior art to the claimed invention.

Herein, "comprising" means that other steps and other components which do not affect the end result can be added.

This term encompasses the terms "consisting of" and "consisting essentially of."

Herein, "effective amount" means an amount of a compound or composition sufficient to significantly induce a positive benefit, preferably an oral health benefit, but low enough to avoid serious side effects, i.e., to provide a reasonable benefit to risk ratio, within the sound judgment of a skilled artisan.

The dentifrice composition of the present invention may be in the form of a toothpaste or dentifrice. The term "dentifrice", as used herein, means paste or gel formulations unless otherwise specified. The dentifrice composition may be in any desired form, such as deep striped, surface striped, multi-layered, having the gel surrounding the paste, or any combination thereof.

The dentifrice composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity.

The term "aqueous carrier" as used herein means any safe and effective materials for use in the compositions of the present invention. Such materials include thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

The present compositions comprise essential components, as well as optional components. The essential and optional components of the compositions of the present invention are described in the following paragraphs.

Polyphosphate Source

The present invention includes a polyphosphate source. Polyphosphates are known to help retard calculus formation. However, it is also known that polyphosphates with an average chain length greater than about 4 will also react with ionic fluoride in oral compositions at ambient temperature and produce monofluorophosphate ions, in addition to altering the pH of the composition. This reaction compromises the efficacy of the oral composition and its ability to provide stable ionic fluoride and polyphosphate to the oral surfaces. It is also known that to have stable polyphosphate, the total water content and pH of the dentifrice composition must be controlled to reduce the hydrolysis of the polyphosphate.

A polyphosphate is generally understood to consist of two or more phosphate molecules arranged primarily in a linear configuration, although some cyclic derivatives may be present. Although pyrophosphates are a polyphosphate, the polyphosphates desired are those having around four or more phosphate molecules. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 6 to about 125, more preferred from about 11 to about 50. Preferred are polyphosphates manufactured by FMC Corporation which are commercially known as Sodaphos (n≈6), Hexaphos (n≈13), and Glass H (n≈21). These polyphosphates may be used alone or in an combination thereof.

The phosphate sources are described in more detail in Kirk & Othmer, *Encyclopedia of Chemical Technology*, Fourth Edition, Volume 18, Wiley-Interscience Publishers (1996). An effective amount of a polyphosphate source will typically be from about 0.1% to about 30%, preferably from about 1% to about 26%, more preferably from about 4% to about 20%, and most preferably from about 5% to about 13%, by weight of the total dentifrice composition.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 40% to about 99%, preferably from about 70% to about 98%, and more preferably from about 90% to about 95%, by weight of the dentifrice composition.

Total Water Content

Water employed in the preparation of commercially suitable oral compositions should preferably be of low ion content and free of organic impurities. In the dentifrice composition, water will generally comprise less than about 10%, and preferably from about 0% to about 6%, by weight of the composition herein. Polyphosphate and actives such as fluoride and stannous are not dissolved in the compositions herein in such low levels of water. However, these ingredients may be dissolved in the present compositions in other low polar solvents, forming non-ionic molecular structures. In either case, the actives remain stable in the compositions during storage. The fluoride ion and the stannous ion if present will be released from their salt forms or non-ionic solution forms only when contacted with saliva and/or water at the time of brushing. Thus there is no need to physically separate the polyphosphate-containing portion of the composition from the ionic active-containing portion of the composition, for example by using a dual compartmented package. In addition, fluoride ion from a variety of sources may be used efficaciously in the present composition; there is no preference for the use of sodium monofluorophosphate as the fluoride ion source that is most compatible with the polyphosphate in the composition as previously described in U.S. Pat. No. 6,190,644, "Dentifrice Compositions Containing Polyphosphate and Sodium Monofluorophosphate."

The amounts of water include the free water which is added plus that which is introduced with other materials, such as with sorbitol, silica, surfactant solutions, and/or color solutions.

Binder System

The dentifrice compositions of the present invention incorporate a binder system comprised of a thickening agent selected from the group consisting of polysaccharides, carbomers, poloxamers, modified celluloses, and mixtures thereof, and at least one humectant. The thickening agent comprises from about 0.05% to about 3%, and preferably from about 0.1% to 1.5%, by weight of the composition. These binder systems provide desirable consistency and gellation to the low water composition. It has previously been known that gelling materials that provide desirable rheology with water and humectant provide generally less satisfactory rheology when the water is not present to activate their gellation binding properties. This is believed to be especially true of glycerin humectant. The binder system may further comprise additional inorganic thickening agents.

A. Thickening Agent

Polysaccharides that are suitable for use herein include carageenans, gellan gum, locust bean gum, xanthan gum, and mixtures thereof. Carageenan is a polysaccharide derived from seaweed and has been known for use as a binder or thickener in toothpastes, see, e.g., U.S. Pat. Nos. 6,187,293 B1 and 6,162,418. There are several types of carageenan that may be distinguished by their seaweed source and/or by their degree of and position of sulfation. Preferred for use in the present invention are kappa carageenans, modified kappa carageenans, iota carageenans, modified iota carageenans, and mixtures thereof. Lambda carageenan is also believed to be suitable for use herein, but is generally less preferred. The gelling temperature for carageenan having kappa as its major ingredient is from about 30 deg C. to about 70 deg C., more preferably from about 40 deg C. to about 65 deg C., most preferred from about 45 deg C. to about 60 deg C. The gelling temperature for carageenan having Iota as its major ingredient is from about 10 deg C. to about 50 deg C., more preferred from about 20 deg C. to about 45 deg C., most preferred from 25 deg C. to about 40 deg C.

Carageenans suitable for use herein include those commercially available from the FMC Company under the series designation "Viscarin," including but not limited to Viscarin TP 329, Viscarin TP 388, and Viscarin TP 389.

The water content for compositions in which the binder system has kappa carageenan as the primary thickening agent is from about 0% to about 10% (w/w), preferably from about 0.1% to about 6% (w/w), and more preferably from about 0.3% to about 5.5%. The water content for compositions in which iota carageenan is the primary thickening agent is from about 0% to about 15% (w/w), preferably from about 0.1% to about 10% (w/w), and more preferably from about 0.3% to about 8%.

Salt impact for kappa and iota carageenan is different. For kappa carageenan, sodium and potassium ion are preferred because they do not significantly impact the viscosity of low water matrix. But for iota carageenan, both sodium and potassium can significantly impact the viscosity of low water matrix, so the addition procedure for these ingredients in low water matrix should be after the iota carageenan has sufficiently gelled up.

Gellan gum is another polysaccharide that is suitable for use herein. It is a polysaccharide aerobically fermented by pseudomonas elodea. It can also form an acceptable low water matrix when it is present at a level of from about 0.1% to about 3%, preferably from about 0.4% to about 1.8% (w/w). The preferred gelling temperature is higher than 40 deg C. To improve the thixotropy and pseudoplastic properties of dentifrice matrix, a combination of gellan gum and carageenan is preferred. When gellan gum meets carageenan at temperatures higher than 40 deg C., these chemicals will form cross-link structure. In this stage, other chemicals such as water, silica and other organic solvents, will be immobilized. The dynamic rate of gelling can be controlled by temperature.

Locust bean gum and xanthan gum are also suitable polysaccharides for use herein. Locust bean gum or xanthan gum as thickening agents can form a stable and acceptable dentifrice matrix when water level is lower than 10% in the composition, but it is believed that they are not as effective as carageenan. Mixing locust gum with xanthan gum is believed to produce higher viscosity structures than if each were to be added alone. Adjusting pH and ion strength is believed to slightly influence the systemic viscosity. The preferred gelling temperature is from about 30 deg C. to about 80 deg C., more preferred from about 40 deg C. to about 70 deg C., and the most preferred from about 45 deg C. to about 60 deg C. for 15 minutes.

Poloxamers are also suitable as thickening agents in the low water matrix herein. Poloxamer is a synthetic block copolymer of ethylene oxide and propylene oxide. It is available in several types. Herein, poloxamer 407 is preferable. It can be partly dissolved in water. When temperature is higher than 65 deg C., it can dissolve in glycerin. Poloxamer 407 is available, for example, from the BASF CORPORATION, New Jersey, USA.

Carbomers are also suitable as thickening agents in a low water matrix, especially in non-water matrix. Normally, the level of carbomer in the composition is from about 0.1% to 2%, more preferably from about 0.2% to about 1.5%, most preferably from about 0.3% to 1.2%. The preferred gelling temperature is from about 15 deg C. to about 40 deg C. In a high water system (e.g., higher than 10%), carbomer can be dissolved in acidic water solution and become viscous at pH around 8.0. But in a low water matrix, the behavior of carbomer is different. It can also gel up when pH is around 3.0 when humectant is glycerin or PEG. The ionic impact is also significant for carbomer, especially from stannous ion. When the matrix contains stannous, adding carbomer in humectant first and letting it unfold are preferred process. Carbomers suitable for use herein include those commercially available from the Goodrich Company under the Carbopol series trade name. Carbopol 956 is particularly suitable for use in the low water matrix of the present compositions. The combination of carageenan and Carbopol 956 is particularly preferred.

Modified celluloses such as hydroxyethyl cellulose are also good thickening agents in low water matrix, especially when combined with carageenan. It can help carageenan to resist the influence from acid, alkali, hypersalt conditions and biodegradation. Since water level is limited in the present compositions, modified hydroxyethyl cellulose with a hydrophobic chain ($C_{12}$–$C_{20}$) are preferred to increase the solubility and hydration of this thickening agent in other low polar solvents, such as glycerin, propylene glycol and PEG.

B. Humectant

The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from about 0.1% to 70%, preferably from about 1% to about 60%, and more preferably from about 15% to 55%, by weight of the composition.

The humectant has a significant impact on the viscosity of low water matrix. For example, when using polysaccharide as the thickening agent in the composition, the viscosity of the matrix will increase when the level of glycerin or polyethylene glycol increases. On the contrary, the viscosity of matrix will decrease when the level of propylene glycol increases in the composition.

C. Inorganic Thickening Agents

The binder system may further comprise additional inorganic thickening agents such as colloidal magnesium aluminum silicate or finely divided silica to further improve texture. Additional inorganic thickening agents if present can be used in an amount from about 0.1% to about 15%, more preferably from about 0.1% to about 5%, by weight of the dentifrice composition.

Ionic Active Ingredient

The dentifrice compositions of the present invention preferably comprise an effective amount of an ionic active ingredient selected from the group consisting of a fluoride ion source, a stannous ion source, a zinc ion source, a copper ion source, and mixtures thereof.

A. Fluoride Ion Source

The fluoride ion source herein is a soluble fluoride source capable of providing free fluoride ions. Soluble fluoride ion sources include sodium fluoride, stannous fluoride, indium fluoride, zinc fluoride, and sodium monofluorophosphate. Sodium fluoride and stannous fluoride are the preferred soluble fluoride ion sources. As noted above, previous disclosures of dentifrices comprising a polyphosphate having a chain length of about 4 or more have indicated that sodium monofluorophosphate is the preferred fluoride ion source. This is because sodium monofluorophosphate has been found to be more stable than other fluoride sources in the presence of a polyphosphate having an average chain length of about 4 or more, as well as in dentifrice compositions containing a relatively higher level of water. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The fluoride ion source in the present compositions is preferably present as a solid dispersion in the composition during storage, prior to actual brushing usage of the composition by a consumer. The level of water in the present compositions is too low to permit the fluoride source to dissolve in the composition during storage. Thus, there is no obvious interaction between the fluoride ion and the polyphosphate or silica during storage, providing a stable composition during storage. When the composition is contacted by saliva and/or water at the time of brushing, the fluoride source will be dispersed and the active ion will be delivered to the oral cavity.

The present compositions may contain a soluble fluoride ion source capable of providing from about 50 ppm to about 3500 ppm, and preferably from about 500 ppm to about 3000 ppm of free fluoride ions. To deliver the desired amount of fluoride ions, fluoride ion source may be present in the total dentifrice composition at an amount of from about 0.1% to about 5%, preferably from about 0.2% to about 1%, and more preferably from about 0.3 to about 0.6%, by weight of the total dentifrice composition.

B. Metal Ion Source

The present invention may comprise a metal ion source that provides stannous ions, zinc ions, copper ions, or mixtures thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions have been found to help in the reduction of gingivitis, plaque, sensitivity, and improved breath benefits. The efficacy of these metal ions in the present compositions is not reduced by the polyphosphate.

Stannous, zinc and copper ions are derived from the metal ion source(s) found in the dentifrice composition in an effective amount. An effective amount is defined as from at least about 1000 ppm metal ion, preferably about 2,000 ppm to about 15,000 ppm. More preferably, metal ions are present in an amount from about 3,000 ppm to about 13,000 ppm and even more preferably from about 4,000 ppm to about 10,000 ppm. This is the total amount of metal ions (stannous, zinc, copper and mixtures thereof) that is present in the compositions for delivery to the tooth surface.

The metal ion sources in the present compositions are preferably not fully ionized in the composition during storage, prior to actual brushing usage of the composition by a consumer. The level of water in the present compositions is too low to permit the metal ion source to dissolve in the composition during storage. But certain salts such as stannous chloride and stannous fluoride, can be solubilized in glycerin or propylene glycol. Both humectants can provide super stability protection for such stannous salts and can also provide a better taste profile than a water (aqueous) solution of stannous. When the composition is contacted by saliva and/or water at the time of brushing, the stannous ion source will be fully ionized and the active ion will be delivered to the oral cavity.

Dentifrices containing stannous salts, particularly stannous fluoride and stannous chloride, are described in U.S. Pat. No. 5,004,597 to Majeti et al. Other descriptions of stannous salt dentifrices are found in U.S. Pat. No. 5,578,293. The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880. Examples of suitable copper ion sources are listed in U.S. Pat. No. 5,534,243.

The combined metal ion source(s) will be present in an amount of from about 0.25% to about 11%, by weight of the final composition. Preferably, the metal ion sources are present in an amount of from about 0.4 to about 7%, more preferably from about 0.45% to about 5%.

Buffering Agent

The present compositions may contain a buffering agent. Buffering agents, as used herein, refer to agents that can be used to adjust the pH of the compositions to a range of about pH 3.0 to about pH 10. The phase of the dentifrice containing stannous will typically have a slurry pH of from about 3.0 to about 5.5, preferably from about 3.25 to about 5, and more preferably from about 3.4 to about 4.5. The phase of the dentifrice containing the polyphosphate will typically have a slurry pH of from about 4.0 to about 10, preferably from about 4.5 to about 8, and more preferably from about 5.0 to about 7.0. A dentifrice containing both stannous and polyphosphate in a single phase will typically have a pH of from about 4 to about 7, preferably from about 4.5 to about 6, and more preferably from about 5 to about 5.5.

The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 0.1% to about 10%, and more preferably from about 0.3% to about 3%, by weight of the present composition. When stannous is present in the composition, preferred buffers are sodium hydroxide, potassium hydroxide, and ammonium hydroxide.

Anticalculus Agents

Optional agents to be used in place of or in combination with the polyphosphate include such materials known to be effective in reducing calcium phosphate mineral deposition related to calculus formation. Agents included are pyrophosphates, tripolyphosphates, synthetic anionic polymers [including polyacrylates and copolymers of maleic anhydride or acid and methyl vinyl ether (e.g., Gantrez), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Abrasive Polishing Materials

An abrasive polishing material may also be included in the toothpaste compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be, used. If the dentifrice composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, "Zeodent", particularly the silica carrying the designation "Zeodent 119."The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658, 553; and 5,716,601. The abrasive in the toothpaste compositions described herein is generally present at a level of from about 6% to about 70% by weight of the composition. Preferably, toothpastes contain from about 10% to about 50% of abrasive, by weight of the dentifrice composition.

Peroxide Source

The present invention may include a peroxide source in the composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Additional Aqueous Carriers

The present compositions may also comprise surfactants, also commonly referred to as sudsing agents. Suitable surfactants are those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The water soluble antimicrobials include quaternary ammonium salts and bis-biquanide salts, among others. Triclosan monophosphate is a preferred additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are examplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey. Other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan is a preferred antimicrobial agent for inclusion in the present compositions. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. The water insoluble antimicrobial agents, water soluble agents, and enzymes may be present in either the first or second dentifrice compositions. The quaternary ammonium agents, stannous salts, and substituted guanidines are preferably present in the second dentifrice composition. These agents may be present at levels of from about 0.01% to about 1.5%, by weight of the dentifrice composition.

An herbal agent, including but not limited to, golden thread extract, honeysuckle extract, and mixtures thereof, may also be present in the compositions herein at levels of from about 0.01% to about 0.05%. Such herbal agents are believed to provide anti-bacterial efficacy. Polyphenols may further be included at levels from about 0.01% to about 2%. A preferred polyphenol is tea polyphenol.

An effective amount of a desensitizing agent may also be incorporated into the present compositions. The desensitizing agents include those selected from alkaline metal salts with a chloride, nitrate sulfate, or acetate of a group II metal or aluminum or polymerizable monomer to occlude the tubules, alkaline metal or ammonium nitrate, ammonium oxylate, citric acid and sodium citrate. Preferred salts are potassium nitrate, potassium citrate, and mixtures thereof. Such desensitizing agents are disclosed in e.g., U.S. Pat. No. 5,718,885.

For compositions that contain stannous, a stain reducing agent such as Plasdone S-630 or aluminum hydrate may further be added to the composition. Plasdone is polyvinyl pyrrolidone (PVP) that can be synthesized by polymerizing vinylpyrrolidone. Commercially, it has been produced as a series of products having mean molecular weights ranging from 10,000 to 700,000. Herein, the low molecular weights and middle molecular weights (from about 10,000 to about 100,000) are preferred. In order to remove stain effectively, the level of PVP is preferably from about 0.5% to about 10%, more preferably from about 1.0% to about 7.0%, and even more preferably from about 1.5% to about 5.0%.

The dentifrice compositions may be a paste, gel, or any configuration or combination thereof. A further embodiment of the present invention includes dual-phase or multi-phase compositions comprising the present low-water compositions as one phase and at least one other separate phase comprising additional dentifrice components to further enhance stability, performance and/or aesthetics of the dentifrice product. For example, a dual phase composition may comprise a first phase comprising the present low-water composition with polyphosphate and ionic active(s) and a separate second phase comprising additional active agents such as bleaching agents, preferably a peroxide source, or a tooth surface conditioning agent to provide improved cleaning, whitening, anti-staining and mouth feel benefits. Examples of tooth conditioning agents are polysiloxanes and modified polysiloxanes, including diorganopolysiloxanes such as polydimethylsiloxane (PDMS); alkyl- and alkoxy-dimethicone copolyols such as C12 to C20 alkyl dimethicone copolyols; and aminoalkylsilicones. These siloxane polymers are described for example in U.S. Pat. Nos. 5,759,523; 6,024,891; 6,123,950; 6,019,962; 6,139,823 all assigned to The Procter & Gamble Company.

The dispenser for the dentifrice compositions may be a tube, pump, or any other container suitable for dispensing toothpaste. In a dual phase oral composition, each oral composition will be contained in a physically separated compartment of a dispenser and dispensed side-by-side.

Methods of Use

In practicing the present invention, the user need only apply the dentifrice composition herein, to the tooth surfaces of a human or lower animal, in the areas desired, in order to obtain a desired effect, e.g., whitening, breath freshening, caries prevention, pain relief, gum health, tartar control, etc. The compositions may also be applied to other oral cavity surfaces, such as the gingival or mucosal tissues, although it is believed that the benefits are best achieved when the dentifrice compositions are applied to the teeth. The dentifrice composition may contact the tooth and/or oral cavity surface either directly, or indirectly; however, it is preferred that the dentifrice composition be directly applied. The dentifrice composition may be applied by any means, but is preferably applied with a brush or by rinsing with a dentifrice slurry.

Examples & Methods of Manufacturing

The following examples further describe and demonstrate embodiments within the scope of the present invention. These examples are given solely for the purpose of illustration and are not to be construed as limitations of the present invention as many variations thereof are possible without departing from the spirit and scope.

EXAMPLES 1–11

The compositions of Examples 1–3 are suitably prepared as follows. Disperse the active(s), sweetener(s), and binder(s) into humectant(s). Heat to between 40 deg C. and 60 deg C. and maintain at this temperature for about 15 to 20 minutes. After the gelling up of binders, cool the vessel to about 40 deg C. before adding the silica. Homogenize the mixture and then vacuumize the vessel. Next, add flavor and SLS solution, and then mix well. Add the polyphosphate into the vessel and mix until homogeneous.

The compositions of Examples 4–11 are suitably prepared as follows. Disperse thickening agents (such as carageenan, xanthan gum, poloxamer or carbopol) into humectant(s). Vacuumize and homogenize for two turnovers. Add water (if present) and vacuumize/stir for 15 minutes to allow binder to be hydrated and unfolded (gelling up). Disperse the active(s), and sweetener(s) into the fluids and mix for 5 minutes. Add buffer and mix for 5 minutes. Homogenize for 2 turnovers and vacuumize again and then add silica; mix for 10 minutes. Add SLS solution and flavor, then mix for 2 minutes. Vacuumize again. Add sodium polyphosphate into the vessel and mix until homogeneous.

| Ingredient | Ex. 1 | Ex. 2 | Ex. 3 | Ex. 4 | Ex. 5 | Ex. 6 |
|---|---|---|---|---|---|---|
| Glass H polyphosphate | 7.000 | 7.000 | 7.000 | 13.000 | 14.030 | 7.000 |
| Sodium Fluoride | 0.243 | 0.321 | 0.243 | — | 0.240 | 0.243 |
| Stannous Fluoride | — | — | — | 0.454 | — | — |
| Zinc Lactate Dihydrate | — | — | — | 2.500 | — | — |
| Zinc Citrate Dihydrate | — | — | — | — | 2.00 | — |
| Sodium Gluconate | — | — | — | 0.652 | 0.650 | — |
| Glycerin | 58.005 | 55.577 | 57.725 | 38.519 | 38.400 | 57.737 |
| PEG-300 | 5.000 | 5.000 | 5.000 | 7.000 | 7.000 | 5.000 |
| Propylene Glycol | — | — | — | 7.000 | 7.000 | — |
| Carageenan | 0.500 | 1.050 | 0.900 | 0.600 | 0.600 | — |
| Xanthan Gum | 0.400 | — | — | 0.350 | 0.350 | 0.200 |
| Poloxamer 407 | — | — | — | — | — | 1.000 |
| Carbomer 956 | — | — | — | — | — | 0.300 |
| Silica abrasive | 20.000 | 20.000 | 20.000 | 25.000 | 25.000 | 20.000 |
| Sodium Lauryl Sulfate (27.9% SLS soln) | 6.000 | — | 6.000 | 2.500 | 2.500 | 5.000 |
| Triclosan | — | — | 0.28 | — | — | — |
| Sodium Lauryl Sulfate, powdered | — | 1.400 | — | — | — | — |
| Betaine | 1.500 | — | 1.500 | — | — | — |
| Flavor | 1.100 | 1.100 | 1.100 | 0.800 | 0.600 | 0.900 |
| Colorant | 0.002 | 0.002 | 0.002 | 0.025 | 0.030 | 0.300 |
| Sodium Saccharin | 0.250 | 0.250 | 0.250 | 0.500 | 0.500 | 0.370 |
| Water | — | 5.300 | — | — | — | 1.250 |
| Trisodium Phosphate | — | 3.000 | — | 1.100 | — | — |
| Sodium Hydroxide | — | — | — | — | — | 0.500 |

| Ingredient | Ex. 7 | Ex. 8 | Ex. 9 | Ex. 10 | Ex. 11 |
|---|---|---|---|---|---|
| Sodium Polyphosphate | 7.000 | 7.000 | 7.000 | 7.000 | 7.000 |
| Carageenan (Viscarin TP 329) | 0.800 | 1.200 | 1.200 | 1.200 | 0.800 |
| Carbomer (Carpobol 956) | 0.300 | — | — | — | 0.300 |
| Glycerin | 52.298 | 51.328 | 51.094 | 58.094 | 58.194 |
| PEG-300 | 5.000 | 5.000 | 5.000 | 5.000 | 5.000 |
| Sodium Fluoride | 0.321 | 0.321 | 0.321 | 0.321 | 0.321 |
| Blue dye | 0.002 | 0.002 | 0.030 | 0.030 | 0.030 |
| Sodium Saccharin | 0.250 | 0.250 | 0.250 | 0.250 | 0.250 |
| Sodium Lauryl Sulfate (27.9% soln.) | 7.000 | 7.000 | 7.000 | 5.000 | 5.000 |
| Silica abrasive | 20.000 | 20.000 | 20.000 | 20.000 | 20.000 |
| Flavor | 1.100 | 1.100 | 1.100 | 1.100 | 1.100 |
| Water | 5.000 | 5.000 | 5.000 | 1.405 | 1.405 |
| NaOH 50% (w/w) solution | 0.929 | 1.649 | 1.405 | 0.600 | 0.600 |
| Tetrapotassium pyrophosphate | — | 0.150 | 0.600 | — | — |

EXAMPLES 12–20

| Ingredient | Ex.12 | Ex. 13 | Ex. 14 |
|---|---|---|---|
| Sodium Fluoride, USP | 0.243 | — | — |
| Stannous Fluoride | — | 0.454 | 0.454 |
| Stannous Chloride, FCC (Dihydrate) | 1.430 | 0.776 | 0.776 |
| Carageenan | 0.400 | 0.400 | 0.300 |
| Xanthan Gum | 0.200 | 0.200 | 0.150 |
| Glycerin USP | 38.120 | 38.564 | 31.019 |
| Propylene Glycol, USP | 9.000 | 9.000 | 9.000 |
| Polyethylene Glycol 300, (PEG) | 9.000 | 9.000 | 9.000 |
| Sodium Polyphosphate, FCC (Glass H) | 13.000 | 13.000 | 20.000 |
| Silica Abrasive | 23.825 | 23.825 | 25.000 |
| Silica Zeodent 165 | 1.000 | 1.000 | 1.000 |
| Sodium Lauryl Sulfate, (SAS) | 1.680 | 1.680 | 1.200 |
| Sodium Hydroxide Solution, FCC (50%) | 0.600 | 0.600 | 0.600 |
| Saccharin, Sodium, USP | 0.400 | 0.400 | 0.400 |
| Flavor | 1.100 | 1.100 | 1.100 |
| FD&C Blue #1 Dye | 0.002 | 0.001 | 0.001 |

| Ingredient | Ex. 15 | Ex. 16 | Ex. 17 |
|---|---|---|---|
| Stannous Fluoride | 0.454 | 0.454 | 0.454 |
| Stannous Chloride, FCC (Dihydrate) | 0.776 | 0.776 | 0.776 |
| Sodium Polyphosphate, FCC (Glass H) | 20.000 | 20.000 | 20.000 |
| Carageenan (Viscarin TP 388) | 0.300 | 0.300 | 0.100 |
| Xanthan Gum | 0.150 | 0.150 | 0.100 |
| Glycerin USP | 31.019 | 29.519 | 31.269 |
| Propylene Glycol, USP | 9.000 | 9.000 | 9.000 |
| Polyethylene Glycol 300, (PEG) | 9.000 | 9.000 | 9.000 |
| Silica Zeodent 119 | — | 12.500 | 12.500 |
| Silica 109 | 25.000 | 12.500 | 12.500 |
| Silica Zeodent 165 | 1.000 | 1.000 | 1.000 |
| Sodium Lauryl Sulfate (SAS) | 1.200 | 1.200 | 1.200 |
| Sodium Hydroxide Solution, FCC (50%) | 0.600 | 0.600 | 0.600 |
| Saccharin, Sodium, USP | 0.400 | 0.400 | 0.400 |
| Flavor | 1.100 | 1.100 | 1.100 |
| FD&C Blue #1 Dye | 0.001 | 0.001 | 0.001 |
| Plasdone S-630 | — | 1.500 | — |

| Ingredient | Ex. 18 | Ex. 19 | Ex. 20 |
|---|---|---|---|
| Stannous Fluoride | 0.454 | 0.454 | 0.454 |
| Stannous Chloride, FCC (Dihydrate) | 0.776 | 0.776 | 0.380 |
| Carageenan (Viscarin TP 389) | 0.300 | — | — |
| Carageenan (Viscarin XP 3531) | — | 0.900 | 0.700 |
| Xanthan Gum | 0.150 | — | — |
| Carpobol 956 | — | — | 0.500 |
| Glycerin USP | 29.519 | 20.468 | 20.764 |
| Propylene Glycol, USP | 9.000 | — | — |
| Polyethylene Glycol 300, (PEG) | 9.000 | 30.000 | 30.000 |
| Sodium Polyphosphate, FCC (Glass H) | 20.000 | 20.000 | 20.000 |
| Silica Abrasive | 25.000 | 25.000 | 25.000 |
| Silica Zeodent 165 | 1.000 | — | — |
| Sodium Lauryl Sulfate (SLS) | 1.200 | 0.500 | 0.500 |
| Sodium Hydroxide Solution, FCC (50%) | 0.600 | 0.600 | 0.600 |
| Saccharin, Sodium, USP | 0.400 | 0.500 | 0.500 |
| Flavor | 1.100 | 0.800 | 0.800 |
| FD&C Blue #1 Dye | 0.001 | 0.002 | 0.002 |
| Plasdone S-630 | 1.500 | — | — |

Examples 12–20 are suitably prepared as follows. Disperse active(s), sweetener(s), and binder(s) into the fluids. Heat the batch to about 40 deg C. to 60 deg C. Maintain at this temperature for about 15 to 20 minutes to allow the binder(s) to be hydrated and gelled up (unfolded). Cool the batch to about 40 deg C. before adding the silica. After homogenizing the mixture and vacuumizing, add buffer and flavor. Then add the polyphosphate. Mix until homogeneous.

Examples 13–16 may also be prepared as follows. Disperse active(s), sweetener(s), and binder(s) into the fluids. Mix them well and add buffer. Stir for 15 minutes to allow the binder(s) to be hydrated and gelled up (unfolded). Add the silica. After homogenizing the mixture and vacuumizing, add solid SLS and flavor. Then add the polyphosphate. Mix until homogeneous.

Examples 17–18 may also be prepared as follows. Disperse binder(s) in humectant(s) and stir for 10 minutes. Then add buffer and stir for 15 minutes to allow the binder(s) to be hydrated and gelled up (unfolded). Disperse salts such as active(s) and sweetener(s) into the fluids. Mix them until homogeneous. Add the silica. After homogenizing the mixture and vacuumizing, add solid SLS and flavor. Then add the polyphosphate. Mix until homogeneous.

Example 19 may also be prepared as follows. Mix glycerin, PEG, dye, active(s) and agitate for 10 minutes. Vacuumize, then add sweetener and binder(s). Homogenize the mixture for two turnovers and vaccumize. Then add NaOH solution and stir for at least 3 minutes. Vacuumize and then add silica abrasive and mix for at least 8 minutes. Vacuumize and then stir for 10 minutes. Add SLS powder and flavor and mix for at least 2 minutes. Then vaccumize and homogenize for two turnovers. Add polyphosphate and mix for at least 5 minutes until homogeneous.

Example 20 may also be prepared as follows. Mix glycerin, PEG and dye and agitate mixture for 5 minutes. Add binder(s). Homogenize the batch for 1 turnover and vacuumize. Mix for 5 minutes. Add NaOH solution. Vacuumize and agitate for 10 minutes. Add active(s). Homogenize for 1 turnover and vacuumize. Add silica abrasive and mix for at least 8 minutes. Add SLS powder and flavor and mix for at least 2 minutes. Then vaccumize and homogenize for two turnovers. Add polyphosphate and mix for at least 5 minutes until homogeneous.

The compositions of the present invention exhibit good viscosity and stability. The Brookfield viscosity of the compositions herein is from about 30 to about 90 BKU after matrix gets to equilibrium. Table 1 shows the viscosity profile versus time of a present composition, Example 12.

TABLE 1

Viscosity profile versus Time at room temperature and 40 deg C.

| Aged Days | 0 | 1 | 2 | 6 | 7 | 8 | 40 | 48 |
|---|---|---|---|---|---|---|---|---|
| Viscosity (BKU) at Room Temp. | 2 | 6 | 10 | 8.6 | 14 | 17 | 48 | 46 |
| Viscosity (BKU) at 40 deg C. | 2 | 33.8 | 74 | 86 | 84 | 88 | 71.4 | 72.6 |

In addition, Tables 2–5 show stability performance for compositions of the present invention. The 40 deg C. temperature refers to a 4 months accelerated stability test while the 60 deg C. temperature refers to 3.5 months accelerated stability test.

The pH of the composition of Example 12 above versus time is shown in Table 2. It can be seen that pH of greater than 5 at 40 deg C. is maintained, which indicates that the composition is mildly acidic and safe for consumer use.

TABLE 2 pH stability versus time

| Days | 0 | 41 | 60 | 80 | 105 | 120 |
|---|---|---|---|---|---|---|
| pH at 40 Deg C. | 5.54 | 5.43 | 5.34 | 5.24 | 5.34 | 5.49 |
| pH at 60 Deg C. | 5.54 | 5.4 | 5.3 | 5.02 | 4.98 | — |

The soluble stannous stability of the composition of Example 12 above versus time is shown in Table 3. It can be seen that the level of soluble stannous remains greater than 65%. This percentage translates to a stannous level of higher than 1200 ppm, which indicates that an effective amount of stannous ion will be available at the time of consumer use.

TABLE 3

Soluble stannous stability versus time

| Days | 0 | 41 | 60 | 80 | 105 | 120 | 135 |
|---|---|---|---|---|---|---|---|
| Soluble Stannous at 40 deg C. (%) | 100 | 84.70 | 84.11 | 75.18 | 76.52 | 78.33 | 66.76 |
| Soluble Stannous at 60 deg C. (%) | 100 | 83.53 | 82.94 | 73.48 | 74.82 | — | — |

The polyphosphate degradation of the composition of Example 12 above versus time is shown in Table 4. It can be seen that the polyphosphate degradation is below 4.21% after 4.5 months storage at 60 deg C. This indicates that polyphosphate is stable in this matrix (the minimum acceptable limit at the same temperature is around 26000 ppm).

TABLE 4

Polyphosphate stability versus time

| Days | 0 | 41 | 60 | 80 | 105 | 120 | 135 |
|---|---|---|---|---|---|---|---|
| Ortho at 40 C. (%) | 1.20 | 1.34 | 1.41 | 1.53 | 1.55 | 1.59 | 2.37 |
| Ortho at 60 C. (%) | 1.20 | 1.46 | 1.54 | 2.50 | 2.75 | 0.00 | 4.21 |

The soluble fluoride stability of the composition of Example 12 above versus time is shown in Table 5. It can be seen that the level of soluble fluoride is higher than 65%. This percentage translates to a fluoride level of higher than 190 ppm. That indicates that an effective amount of fluoride ion will be available at the time of consumer use.

TABLE 5

Soluble fluoride stability versus time

| Timing (Days) | 0 | 41 | 60 | 80 | 105 | 120 | 135 |
|---|---|---|---|---|---|---|---|
| Soluble fluoride at 40 C. (%) | 100 | 97.14 | 93.06 | 88.57 | 89.80 | 91.84 | 90.61 |
| Soluble fluoride at 60 C. (%) | 100 | 89.80 | 88.57 | 82.86 | 79.59 | 0.00 | 78.78 |

It is understood that the examples and embodiments described herein are for illustrative purposes only and that various modifications or changes in light thereof will be suggested to one skilled in the art without departing from the scope of the present invention.

What is claimed is:

1. A dentifrice composition comprising in a single phase:
   a. from about 0.1% to about 30% of one or more linear polyphosphates having an average chain length of about 4 or more, wherein said polyphosphate is water soluble and susceptible to hydrolysis;
   b. an ionic active ingredient selected from the group consisting of a fluoride ion source, a stannous ion source, a zinc ion source, a copper ion source, and mixtures thereof, wherein the ionic active ingredient is present as a solid dispersion in the composition and delivers an effective amount of ionic active when solubilized;
   c. a binder system comprised of from (i) about 0.05% to about 3% of a thickening agent selected from the group consisting of polysaccharides, carbomers, poloxamers, modified celluloses, and mixtures thereof; and (ii) from about 0.1% to about 70% of at least one humectant;
   wherein the dentifrice composition has an effective amount of water of up to about 9%.

2. The composition of claim 1 wherein the polysaccharide is selected from the group consisting of carageenan, gellan gum, locust bean gum, xanthan gum, and mixtures thereof.

3. The composition of claim 2 wherein the thickening agent comprises a mixture of a carageenan and a carbomer.

4. The composition of claim 2 wherein the thickening agent comprises a mixture of a poloxamer, a carbomer, and xanthan gum.

5. The composition of claim 1 wherein the humectant is selected from the group consisting of glycerin, polyethylene glycol, polypropylene glycol, and mixtures thereof.

6. The composition of claim 1 wherein the polyphosphate is selected from the group consisting of linear glassy polyphosphates having the formula $$XO(XPO_3)_nX$$

wherein X is sodium or potassium and n averages from about 6 to about 50.

7. The composition of claim 6 wherein the polyphosphate has an average chain length of about 21.

8. The composition of claim 1 further comprising aqueous carriers which are materials selected from the groups consisting of additional inorganic thickening agents, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

9. A method of stabilizing a dentifrice composition comprising at least one ingredient selected from water-soluble and hydrolysis-susceptible linear polyphosphates, a fluoride ion source, a stannous ion source, a zinc ion source and a copper ion source, the method comprising:
   (a) providing the composition with a binder system comprised of (i) from about 0.05% to about 3% of a thickening agent selected from the group consisting of polysaccharides, carbomers, poloxamers, modified celluloses, and mixtures thereof; and (ii) from about 0.1% to about 70% of at least one humectant;
   wherein the ion sources are present as solid dispersions in the composition, and wherein the dentifrice composition has an effective amount of water of up to about 9%.

10. A binder system for a single phase dentifrice composition comprising ionic active ingredients, the binder system comprised of (i) from about 0.05% to about 3% of a thickening agent selected from the group consisting of polysaccharides, carbomers, poloxamers, modified celluloses, and mixtures thereof; and (ii) from about 0.1% to about 70% of at least one humectant;
   wherein the ionic ingredients are present as solid dispersions in the composition, and wherein the dentifrice composition has an effective amount of water of up to about 9%.

11. A dentifrice composition comprising a first phase and a second phase, wherein the first phase comprises a composition having an effective amount of water of up to about 9% and comprising
   a. from about 0.1% to about 30% of one or more linear polyphosphates having an average chain length of about 4 or more, wherein said polyphosphate is water soluble and susceptible to hydrolysis;

b. an ionic active ingredient selected from the group consisting of a fluoride ion source, a stannous ion source, a zinc ion source, a copper ion source, and mixtures thereof, wherein the ionic active ingredient is present as a solid dispersion in the composition and delivers an effective amount of ionic active when solubilized;

c. a binder system comprised of from (i) about 0.05% to about 3% of a thickening agent selected from the group consisting of polysaccharides, carbomers, poloxamers, modified celluloses, and mixtures thereof; and (ii) from about 0.1% to about 70% of at least one humectant;

wherein the second phase comprises a composition comprising an oral care active selected from the group consisting of a bleaching agent, a whitening agent, a tooth surface conditioning agent, and mixtures thereof.

* * * * *